United States Patent
Tamura et al.

(10) Patent No.: US 7,943,720 B2
(45) Date of Patent: May 17, 2011

(54) METHOD OF MANUFACTURING PURIFIED PRODUCTS OF LIQUID MEDIUM-CHAIN ALKYL-MODIFIED POLYDIMETHYSILOXANE AND COSMETICS PREPARED THEREFROM

(75) Inventors: Seiki Tamura, Chiba (JP); Yasuhiro Kaneta, Chiba (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 1217 days.

(21) Appl. No.: 10/598,108

(22) PCT Filed: Feb. 16, 2005

(86) PCT No.: PCT/JP2005/002840
§ 371 (c)(1),
(2), (4) Date: Aug. 17, 2006

(87) PCT Pub. No.: WO2005/085325
PCT Pub. Date: Sep. 15, 2005

(65) Prior Publication Data
US 2007/0166264 A1    Jul. 19, 2007

(30) Foreign Application Priority Data
Feb. 17, 2004  (JP) .................... 2004-040120

(51) Int. Cl.
*C08G 77/08*  (2006.01)
(52) U.S. Cl. .............. 528/15; 528/31; 424/401
(58) Field of Classification Search .......... 528/31, 528/15; 424/401
See application file for complete search history.

(56) References Cited

U.S. PATENT DOCUMENTS

| 3,671,433 A * | 6/1972 | Brenner ............ 508/212 |
| 4,417,068 A | 11/1983 | Kollmeire et al. |
| 4,640,792 A * | 2/1987 | Groenhof et al. ......... 252/78.3 |
| 5,413,781 A * | 5/1995 | Giwa-Agbomeirele et al. ............ 424/78.03 |
| 6,395,704 B1 * | 5/2002 | Branlard et al. ............ 512/1 |
| 6,437,163 B1 * | 8/2002 | Branlard et al. .......... 556/450 |
| 6,784,271 B2 | 8/2004 | Nakanishi |
| 6,803,440 B2 * | 10/2004 | Marko et al. .............. 528/14 |

FOREIGN PATENT DOCUMENTS

| GB | 1503670 | 3/1978 |
| JP | 51102019 | 9/1976 |
| JP | 58046094 | 3/1983 |
| JP | 4046933 | 2/1992 |
| JP | 2003012466 | 1/2003 |
| JP | 2003-048813 | * 2/2003 |
| JP | 2003048813 | 2/2003 |
| JP | 2003-306550 | * 10/2003 |
| WO | WO02/055588 | 7/2002 |

OTHER PUBLICATIONS

Machine generated translation of JP 2003-306550, Oct. 31, 2003.*
English language abstract for JP4046933 extracted from espacenet.com database, Jan. 12, 2007.
English language translation of application and English language abstract for JP2003012466 extracted from Searching PAJ.
English language translation of application and English language abstract for JP2003048813 extracted from Searching PAJ.
English language abstract for WO 02/055588 extracted from espacenet.com database, May 27, 2007.

* cited by examiner

*Primary Examiner* — Margaret G Moore
(74) *Attorney, Agent, or Firm* — Howard & Howard Attorneys PLLC

(57) ABSTRACT

A method of manufacturing a purified product of a liquid medium-chain alkyl-modified polydimethylsiloxane that is free of a specific (unpleasant) odor and is practically odorless, the method comprising the steps of: [A] synthesizing a liquid medium-chain alkyl-modified polydimethylsiloxane by carrying out a hydrosilylation reaction between a hydrosilyl-containing polydimethylsiloxane and an α-olefin with 4 to 18 carbon atoms; and [B] subjecting a crude product of the liquid medium-chain alkyl-modified polydimethylsiloxane obtained in preceding step [A] to an odor-removing treatment by conducting a hydrogenation reaction which is carried out in the presence of a hydrogenation catalyst.

17 Claims, No Drawings

METHOD OF MANUFACTURING PURIFIED PRODUCTS OF LIQUID MEDIUM-CHAIN ALKYL-MODIFIED POLYDIMETHYSILOXANE AND COSMETICS PREPARED THEREFROM

RELATED APPLICATIONS

This application claims priority to and all the advantages of International Patent Application No. PCT/JP2004/002840, filed on Feb. 16, 2005, which claims priority to Japanese Patent Application No. JP 2004-040120, filed on Feb. 17, 2004.

TECHNICAL FIELD

This invention relates to a method of manufacturing a purified product of a liquid medium-chain alkyl-modified polydimethylsiloxane and to cosmetics made therefrom, in particular, to a method of manufacturing a purified product of a liquid medium-chain alkyl-modified polydimethylsiloxane by subjecting a crude liquid medium-chain alkyl-modified polydimethylsiloxane to an odor-removing treatment by a hydrogenation reaction. The invention also relates to a cosmetic material that contains an odorless purified product obtained by the aforementioned method.

BACKGROUND ART

A polydimethylsiloxane modified with alkyl groups (except for methyl groups) combines properties of both silicone and alkane and is characterized by excellent characteristics, such as lubricity, humectant (vapor obstructive) properties, adsorption residual properties, etc.

Alkyl-modified dimethylpolysiloxanes, especially those liquid polydimethylsiloxanes that are modified with alkyl groups that contain 4 to 18 carbon atoms (hereinafter referred to as "medium-chain alkyl groups"), are superior in their handling properties to wax-type dimethylsiloxanes modified with long-chain alkyl groups, possess excellent emulsifiability and emulsion stability when used as oiling agents in emulsification systems of cosmetic products, and demonstrate good feeling of application and water repellency. Therefore, it is expected that such alkyl-modified dimethylsiloxanes will find wide application in the manufacture of shampoos, rinsing, hair-treatment, and sun-screen products, moisturization creams, or similar products (see, e.g., Japanese Unexamined Patent Application Publications [Kokai] 2003-12466 and 2003-48813).

Generally, alkyl-modified polydimethylsiloxane is synthesized by causing a hydrosilylation reaction (addition reaction) between polydimethylsiloxane having hydrosilyl groups (Si—H groups) and α-olefin in the presence of a platinum catalyst.

However, an alkyl-modified polydimethylsiloxane synthesized by the above-described method is characterized by a specific (rather unpleasant) odor. One of the sources of this odor is α-olefin, which is used in an excessive amount during synthesis, remains as a residue in the reaction product (crude product), and generates an odor when oxidized.

Since the number of carbon atoms in the α-olefin used for the reaction during synthesis of the liquid polydimethylsiloxane modified with the medium-chain alkyl group is relatively small, i.e., 4 to 18, even though some amount of such α-olefin remains in the reaction product (crude product), it can be removed from the product by heating in vacuum.

However, even if the α-olefin is completely removed (below the limit of detection) from the product (i.e., liquid alkyl-modified polydimethylsiloxane), an unpleasant odor is still sensed and, moreover, this unpleasant odor tends to increase with time.

If the problem associated with such an unpleasant odor is not solved, the liquid polydimethylsiloxane modified with the medium-chain alkyl cannot be used in cosmetics since this odor will negatively affect the quality of scent, and this will significantly limit the scope of practical application of such products.

The present invention is based on the above information.

The first object of the present invention is to provide a method of manufacturing a purified product of a liquid medium-chain alkyl-modified polydimethylsiloxane that is free of a specific (unpleasant) odor and that is practically odorless.

The second object of the present invention is to provide a method of manufacturing a purified product of a liquid medium-chain alkyl-modified polydimethylsiloxane that is odorless and does not exude an unpleasant odor with the lapse of time.

The third object of the present invention is to provide cosmetics that do not produce a specific (unpleasant) odor due to the presence of the liquid alkyl-modified polydimethylsiloxane.

DISCLOSURE OF INVENTION

The manufacturing method of the present invention comprises:

[A] synthesizing a liquid medium-chain alkyl-modified polydimethylsiloxane represented by general formula (2), given below, by carrying out a hydrosilylation reaction between a hydrosilyl-containing polydimethylsiloxane and an α-olefin with 4 to 18 carbon atoms; and

[B] subjecting a crude product of the liquid medium-chain alkyl-modified polydimethylsiloxane obtained in preceding step [A] to odor-removing treatment by conducting a hydrogenation reaction that is carried out in the presence of a hydrogenation catalyst:

General Formula (1)

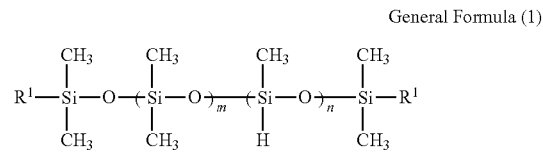

(where $R^1$ represents a hydrogen atom or a methyl group; "m" is an integer from 0 to 6;
and "n" is an integer from 0 to 3. However, when "n" is 0, then at least one $R^1$ represents a hydrogen atom).

General Formula (2)

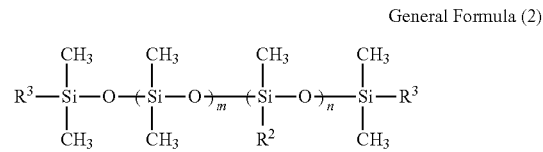

(where $R^2$ represents an alkyl group with 4 to 18 carbon atoms; both $R^3$ are groups represented by $R^2$ above or a methyl group; and "m" and "n" are the same numbers as defined above for general formula (1). However, when "n" is 0, at least one $R^3$ is the same group as defined for $R^2$).

In step [A] of the method of the invention, it is preferable to synthesize a liquid medium-chain alkyl-modified polydimethylsiloxane of general formula (3), given below, by conducting a hydrosilylation reaction between 1,1,1,3,5,5,5-heptamethyltrisiloxane and an α-olefin having 4 to 18 carbon atoms.

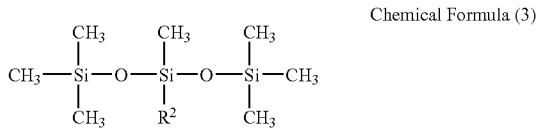

Chemical Formula (3)

[where $R^2$ is the same as defined above for general formula (2)].

It is desirable that α-olefin, which is supplied to the hydrosilylation reaction of step [A], contain 4 to 12 carbon atoms. Furthermore, it is more preferable to use α-olefin with 6 to 12 carbon atoms. It is even more preferable to use α-olefin with 6 to 10 carbon atoms. It is most preferable to use α-olefin with 8 carbon atoms.

In processes that are carried out prior to and/or after step [B] in the method of the invention, it is recommended to remove residual light components from the crude product of the hydrogenation of the liquid medium-chain alkyl-modified polydimethylsiloxane and/or the product of a hydrogenation reaction by bringing these products into contact with gaseous nitrogen under conditions of reduced pressure.

The cosmetics of the present invention are characterized by containing purified products of the liquid medium-chain alkyl-modified polydimethylsiloxane obtained by the method of the invention.

It is recommended that the cosmetics of the invention comprise: (a) 0.1 to 95 mass % of an oiling agent which is the liquid medium-chain alkyl-modified polydimethylsiloxane obtained by the method of the invention; (b) 0.1 to 25 mass % of a surface-active agent with the value of HLB equal to or below 7; and (c) 4.9 to 95 mass % of water.

Effects of Invention (1) The method of the invention makes it possible to manufacture a purified product of a liquid medium-chain alkyl-modified polydimethylsiloxane that is free of a specific (unpleasant) odor and is practically odorless.
(2) The method of the invention makes it possible to manufacture a purified product of a liquid medium-chain alkyl-modified polydimethylsiloxane that is free of a specific (unpleasant) odor and that remains odorless with the lapse of time.
(3) The cosmetic product of this invention does not emit a specific (unpleasant) odor caused by the presence of the liquid medium-chain alkyl-modified polydimethylsiloxane.

DETAILED DESCRIPTION OF THE INVENTION

The invention will be further explained in more detail.
The method of the present invention comprises a process of manufacturing a purified liquid medium-chain alkyl-modified polydimethylsiloxane by step [A] synthesizing a liquid medium-chain alkyl-modified polydimethylsiloxane and step [B] subjecting the crude liquid medium-chain alkyl-modified polydimethylsiloxane obtained in step [A] to an odor-removing treatment by conducting a hydrogenation reaction. The purified product obtained by the method of the invention is a medium-chain alkyl-modified polydimethylsiloxane in a "liquid" form. The term "liquid" means that at a temperature of 20° C., the product has fluidity.

<Step [A]>

Step [A] is a process of synthesis of a liquid medium-chain alkyl-modified polydimethylsiloxane of aforementioned general formula (2) by carrying out a hydrosilylation reaction between a hydrosilyl-containing polydimethylsiloxane of aforementioned general formula (1) and α-olefin having 4 to 18 carbon atoms.

In above-mentioned general formula (1) that represents a hydrosilyl-containing polydimethylsiloxane supplied to the hydrosilylation reaction, $R^1$ designates a hydrogen atom or a methyl group; "m" is an integer from 0 to 6; and "n" is an integer from 0 to 3. However, when "n" is equal to 0, at least one $R^1$ is a hydrogen atom.

A preferable example of the hydrosilyl-containing polydimethylsiloxane is 1,1,1,3,5,5,5-heptamethyltrisiloxane.

It is preferable that the α-olefin supplied to the hydrosilylation reaction contain 4 to 18 carbon atoms, preferably 4 to 12 carbon atoms, more preferably 6 to 12 carbon atoms, still further preferably 6 to 10 carbon atoms, and most preferably 8 carbon atoms.

If the number of carbon atoms in the α-olefin is below the recommended lower limit, it would be impossible to synthesize an alkyl-modified polydimethylsiloxane with a sufficient effect of modification by alkyl. On the other hand, if the number of carbon atoms in the α-olefin exceeds the recommended upper limit, it would be impossible to obtain a liquid alkyl-modified polydimethylsiloxane of excellent handleability and stability in an emulsion state when the product is used as an oiling agent for emulsification.

When the α-olefin that contains 6 to 10 carbon atoms, especially 8 carbon atoms, is used as an oiling agent in preparation of the emulsion, it becomes possible to synthesize liquid medium-chain alkyl-modified polydimethylsiloxane with excellent emulsion stability, pleasant feel of application, and water-repellant properties.

From the same point of view, it is preferable that the α-olefin supplied to the hydrosilylation reaction have non-branched linear molecular chains and preferably comprise 1-octene.

The hydrosilylation reaction for synthesizing the liquid medium-chain alkyl-modified polydimethylsiloxane can be performed by conventional methods with or without a solvent.

Solvents suitable for the reaction may be represented by ethanol, isopropyl alcohol, or similar alcohols, by toluene, xylene, or similar aromatic hydrocarbons, by dioxane, THF, or similar ethers, by aliphatic hydrocarbons, chlorinated hydrocarbons, or similar organic solvents.

Although a hydrosilylation reaction may be performed without the presence of a catalyst, the presence of a catalyst is preferable for shortening the reaction time and for the possibility of conducting the reaction at low temperatures. Catalysts suitable for the reaction are exemplified by platinum, ruthenium, rhodium, palladium, osmium, iridium, or similar compounds. Most preferable of these are platinum-type compounds since they possess a high catalytic activity. Examples of platinum-type catalysts are the following: chloroplatinic acid; metal platinum; metal platinum on a carrier such as alumina, silica, carbon black, etc.; platinum-vinyl siloxane complexes, platinum-phosphine complexes, platinum-phosphite complexes, and platinum alcoholate catalysts, or similar complexes. When platinum-type catalysts are used, they should contain metal platinum in an amount of 0.5 to 100 ppm.

Usually the hydrosilylation reaction should be carried out at a temperature of 50 to 150° C., and the reaction time is usually in the range of 10 minutes to 24 hours, preferably 1 to 10 hours.

The liquid medium-chain alkyl-modified polydimethylsiloxane of general formula (2) synthesized by the hydrosilylation reaction is a crude product.

In general formula (2), which corresponds to the aforementioned medium-chain alkyl-modified polydimethylsiloxane, $R^2$ is an alkyl group with the number of carbon atoms originating from α-olefin that should be in the range of 4 to 18, preferably 4 to 12, more preferably 6 to 12, even more preferably 6 to 10, and most preferably 8. In the above formula, $R^3$ designates the same groups as defined above for $R^2$ or methyl groups; and "m" and "n" are the same numbers as defined above for general formula (1). When "n" is equal to 0, at least one $R^3$ is a group represented by $R^2$.

A suitable example of a liquid medium-chain alkyl-modified polydimethylsiloxane is a modified polydimethylsiloxane shown by the above-mentioned general formula (3).

The liquid medium-chain alkyl-modified polydimethylsiloxane of general formula (3) is synthesized by causing a hydrosilylation reaction between the aforementioned α-olefin and 1,1,1,3,5,5,5-heptamethyltrisiloxane (preferably hydrosilyl-containing polydimethylsiloxane).

In the aforementioned general formula (3), $R^2$ is the same as defined above for general formula (2).

Specific examples of the liquid medium-chain alkyl-modified polydimethylsiloxane represented by the aforementioned general formula (3) can be exemplified by compounds which are expressed by formulae (I) through (VII).

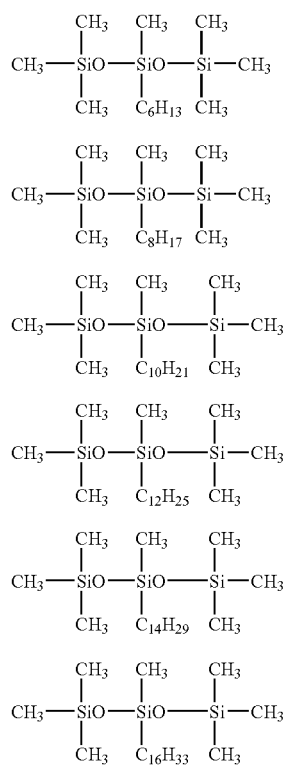

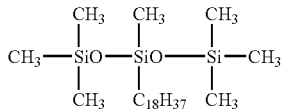

An internal rearrangement of double bonds in the α-olefin may occur in the hydrosilylation process as a side reaction that may produce by products that do not participate in an addition reaction to hydrosilyl groups.

On the other hand, the target product becomes unstable if it contains highly reactive hydrosilyl groups. Therefore, generally the charges of α-olefins and hydrosilyl-containing polydimethylsiloxane and α-olefin are adjusted so as to obtain an excess of unsaturated groups as compared to hydrosilyl groups. For this reason, the crude product of the liquid medium-chain alkyl-modified polydimethylsiloxane obtained as a result of the hydrosilylation reaction will inevitably contain unreacted α-olefins and internally rearranged olefins. However, since α-olefin used in the method of the present invention has a relatively low number of carbon atoms (i.e., has a relatively low boiling point), the aforementioned by-products can be easily removed.

Since the hydrosilyl-containing polydimethylsiloxane used in the method of the invention has a relatively low molecular weight and therefore high volatility, upon completion of the hydrosilylation reaction by adding it in an excessive amount, the light components with the unreacted hydrosilyl-containing polydimethylsiloxane and the internally rearranged olefins can be removed.

The following description relates to the process of removal (stripping step) of light components that contain the unreacted α-olefins or hydrosilyl-containing polydimethylsiloxanes, as well as the internally rearranged olefins.

<Step [B]>

Step [B] is a process of deodorization by subjecting the crude product of the liquid medium-chain alkyl-modified polydimethylsiloxane obtained in step [A] to hydrogenation in the presence of a hydrogenation catalyst.

Deodorization treatment by means of the hydrogenation reaction is performed in the presence of a hydrogenation catalyst.

Hydrogenation catalysts suitable for the aforementioned reaction can be exemplified by nickel, palladium, platinum, rhodium, cobalt, chromium, copper, iron, or compounds of the aforementioned metals. The catalysts may be supported by arbitrary carriers such as activated carbon, silica, silica alumina, alumina, zeolite, etc. Moreover, the platinum catalyst used in the synthetic process (hydrosilylation reaction) can also be used as it is. The hydrogenation catalysts can be used individually or in combinations of two or more.

The hydrogenation reaction can be carried out with or without a solvent.

A solvent that is arbitrarily used in the hydrogenation reaction is selected from those solvents that are neutral to the reaction. The following are specific examples of such solvents: ethanol and isopropyl alcohol, or similar alcohols; dioxane, THF, or similar ethers; aliphatic hydrocarbons, chlorinated hydrocarbons, water, etc. These solvents can be used individually or in combinations of two or more. Moreover, the solvent that is used in the synthesis (i.e., in the hydrosilylation reaction) and constitutes a component of the reaction solution can also be used as it is.

The hydrogenation reaction can be performed under normal pressure or increased pressure. In fact, the reaction is carried out in pressurized hydrogen (hydrogen pressure is in the range of 0.1 to 20 MPa, i.e., 1 to 200 kg/cm$^2$). The reaction is carried out at a temperature of 0 to 200° C. A temperature of 50 to 170° C. is most suitable for shortening the reaction time.

The hydrogenation reaction can be carried out as a batch process or as a continuous process. In a batch process, the reaction time depends on factors such as the amount of the catalyst, reaction temperatures, etc., but, in general, the reaction continues for 3 to 12 hours.

In a batch process, the terminal point of a hydrogenation reaction can be considered to be the time during which the decrease in pressure of hydrogen is no longer observed after the reaction is continued for an additional 1 to 2 hours. If hydrogen pressure decreases in the course of the reaction, it is recommended to repeat the introduction of hydrogen and to maintain it under increased pressure in order to shorten the reaction time.

After completion of the hydrogenation reaction, the hydrogenation reaction catalyst (which is a hydrosilation catalyst if it is present in the reaction system) is separated in a pressurized nitrogenous atmosphere by using filter paper, diatomaceous earth, or activated carbon.

<Stripping Process>

In the method of the invention, prior to and/or after step [B], it is desirable to subject a crude product of the liquid medium-chain alkyl-modified polydimethylsiloxane and/or a product of hydrogenation, to stripping of light substances by bringing the product in contact with gaseous nitrogen and distilling the substances under reduced pressure.

In the context of the present invention, in addition to reaction solvents used in the hydrosilylation reaction (i.e., in step [A] and/or in hydrogenation reaction (step [B]), the term "light substances", which are distilled by the stripping process, also covers the unreacted α-olefin or hydrosilyl-containing polydimethylsiloxane that is used in an excessive amount and remains in the reaction product after step [A], as well as the internally rearranged olefins and olefin hydrates that constitute by-products.

A stripping process (distillation of light substances) may be carried out prior to step [B] by treating the crude product of the liquid medium-chain alkyl-modified polydimethylsiloxane, or after completion of step [B] by treating the product of hydrogenation of the liquid medium-chain alkyl-modified polydimethylsiloxane. If necessary, the stripping process can be carried out in both cases, i.e., prior to and after step [B].

According to one example of distillation of light substances, the crude product or product of hydrogenation which contains a light substance is loaded into a flask equipped with a reflux cooling pipe, nitrogen supply pipe, etc. During supply of nitrogen to the flask, pressure is reduced, and temperature is increased. During distillation of light substances, however, pressure and temperature are kept constant.

In the method of the invention, the reduced pressure conditions correspond to from 0.1 to 10.0 KPa, heating conditions correspond to from 50 to 170° C., and treatment time may be in the range of 10 min. to 24 hours.

<Purified Product of Liquid Medium-Chain Alkyl-Modified Polydimethylsiloxane>

A purified product of the liquid medium-chain alkyl-modified polydimethylsiloxane is obtained by the method of the present invention that consists of aforementioned step [A], step [B], and, if necessary, the stripping process.

If the purified product of the liquid medium-chain alkyl-modified polydimethylsiloxane obtained by the method of the present invention is emulsified, the obtained emulsion may remain stable with time and in a wide range of temperatures (preferably in a low-temperature environment, i.e., equal to or below 10° C.).

A freshly prepared emulsion produces a clean feeling of use and, when applied, demonstrates good spreadability and the ability to form a uniform coating film. Since the aforementioned coating film possesses good water repellence, it imparts a long-lasting effect to cosmetic substances that contain the emulsion.

After the aforementioned purified product is subjected to an odor-removing treatment by the hydrogenation reaction performed in step [B], the product is freed from a specific (unpleasant) odor and becomes practically odorless and, therefore, suitable for blending with various raw materials for cosmetics.

A product most suitable for use as a raw material for cosmetic substances among the purified products obtained by the method of the present invention is a liquid medium-chain alkyl-modified polydimethylsiloxane represented by above-mentioned general formula (3).

<Cosmetics>

Cosmetics that pertain to the present invention are characterized by containing purified products of liquid medium-chain alkyl-modified polydimethylsiloxane obtained by the method of the present invention.

Regarding the cosmetics of this invention, it is recommended that it consist of a water-in-oil type emulsion in which the purified product of the invention is used as an oiling agent (oily component).

A suitable cosmetic that constitutes a water-in-oil type emulsion may be composed of the following components:
(a) 0.1 to 95 mass % of an oiling agent that contains the liquid medium-chain alkyl-modified polydimethylsiloxane obtained by the method of the present invention;
(b) 0.1 to 25 mass % of a surface-active agent with HLB equal to or below 7; and
(c) 4.9 to 95 mass % of water.

Hereinafter, the cosmetics of the aforementioned type will be referred to as "water-in-oil type emulsified cosmetics".

<Component (a)>

Component (a) of the water-in-oil type emulsified cosmetic of the invention is an indispensable component of the liquid medium-chain alkyl-modified polydimethylsiloxane obtained by the method of the invention [hereinafter referred to as "a purified product of alkyl-modified silicone (a1)"]. The use of other oiling constituents is arbitrary.

A volatile silicone [hereinafter referred to as "another oiling constituent"] also may be used along with the purified product of alkyl-modified silicone (a1) as a constituent of component (a). The aforementioned volatile silicone can be represented by a cyclic silicone (a2) of general formula (4) given below.

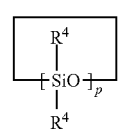

Formula (4)

In general formula (4), each $R^4$ may independently designate a hydrocarbon group of formula $C_xH_{2x+1}$ (where "x" is 1 or an integer greater than 1), a hydrogen atom, and a hydroxyl- or phenyl-containing group, a phenyl or methyl group being preferable; "p" is an integer between 3 and 12, preferably between 4 and 6.

Specific examples of preferable cyclic silicones (a2) are compounds shown below by their respective formulae (VIII)-(X):

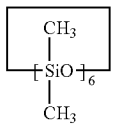

(VIII)

dodecamethyl cyclohexasiloxane

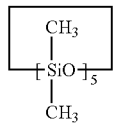

(IX)

decamethyl cyclopentasiloxane

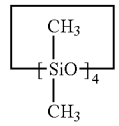

(X)

octamethyl cyclotetrasiloxane

Another oily constituent of component (a) may be a chain-type silicone (a3) of the type shown by the following general formula (5):

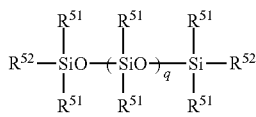

General Formula (5)

In above formula (5), each $R^{51}$ may independently designate: a trimethylsiloxy group or a methyl- or phenyl-containing group. A phenyl-containing group may be represented by a phenyl group, tolyl group, xylyl group, or a similar aryl group; or a benzyl group, phenethyl group, or a similar aralkyl group. Use of a methyl- or phenyl-containing group is preferable.

In the above formula (5), each $R^{52}$ may independently designate a group defined above for $R^{51}$ (such as a methyl-, phenyl-containing group or a trimethylsiloxy group), a hydrogen atom, a hydroxyl group, a vinyl group or an alkoxy group with 1 to 4 carbon atoms). Methyl groups are preferable.

The repetition index "q", which is 0 or an integer higher than 0, can be used for selecting chain-type silicones (a3) of various degrees of polymerization, depending on required characteristics of the water-in-oil type emulsified cosmetic.

A suitable chain-type silicone (a3) may be represented by a dimethylpolysiloxane of formula (XI), methylphenylpolysiloxane of formula (XII), 1,3,3,5-tetramethyl-1,1,5,5-tetraphenyl trisiloxane, and 1,3,5-trimethyl-1,1,3,5,5-pentaphenyltrisiloxane.

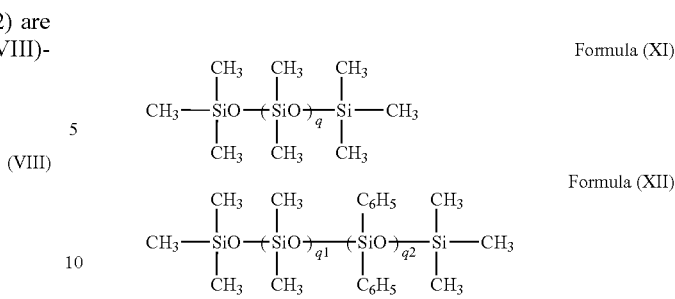

(where "q1" and "q2" are 0 or integers higher than 0).

Another oiling constituent of component (a) can be exemplified by silicone oil other than cyclic silicone (a2) and chain-type silicone (a3), a liquid isoparaffin-type hydrocarbon, an ester-type hydrocarbon, paraffin-type hydrocarbon, squalane, lanolin derivative, higher alcohol, avocado oil, palm oil, beef tallow, jojoba oil, polyalkylene glycol polyether, and its carboxylic-acid oligoester compound, terpene hydrocarbon oil, etc.

The isoparaffin-type hydrocarbon may be one that has a boiling point under normal pressure in the range of 60 to 260° C. Examples of such isoparaffin-type hydrocarbons are the following: Isopar®-A -C, -D, -E, -G, -H, -K, -L and -M of Exxon Corp.; Shelsol®-71 of Shell Corp.; Soltol® 100, 130, and 220 of Phillips Petroleum Corp.

The ester-type hydrocarbon is exemplified by isopropyl myristate, isopropyl palmitate, cetyl 2-ethylhexanate, isocetyl 2-ethylhexanate, glyceryl tri-2-ethylhexanate, trimethylolpropane tri-2-ethylhexanate, glyceryl (tricapril-caprate), glyceryl triisostearate, 2-ethylhexyl hydroxystearate, pentaerythritol tetra (2-ethylhexanoate, neopentylglycol dicaprylate, octyldodecyl myristate, octyl palmitate, isooctyl palmitate, octyl stearate, isooctyl stearate, butyl stearate, myristyl myristate, stearyl stearate, isononyl isononate, isodecyl isononate, isotridecyl isononate, 2-ethylhexyl isononate, isopropyl isostearate, 2-hexyldecyl isostearate, propyleneglycol isostearate, polyethyleneglycol diisostearate, pentaerythritol tetraisostearate, octyl isopalmitate, isocetyl pivalate, octyldodecyl pivalate, octyldodecyl lactate, diisobutyl adipate, di-2-ethylhexyl succinate, neopentylglycol di-2-ethylhexanoate, polyglyceryl monoisostearate, polyglyceryl diisostearate, polyglyceryl triisostearate, polyglyceryl tetraisostearate, hexyl laurate, diisopropyl dimerate, etc.

When a purified product of alkyl-modified silicone (a1) component (a) of the water-in-oil type emulsified cosmetic of the invention also contains another oiling agent (oiling constituent), the aforementioned purified product (a1) should be used in an amount of more than 0.1 mass %, preferably more than 1 mass %, and even more preferably more than 5 mass % per total content of component (a).

If the purified product of alkyl-modified silicone (a1) is used only in a microscopic amount, as compared to the total amount of component (a), the prepared emulsified cosmetic will not possess a pleasant feel of use and sufficient spreadability, while the applied film of the cosmetic will not demonstrate sufficient resistance to water and water-repellent properties.

When cyclic silicone (a2) is used as a constituent of component (a), it should be added in an amount of 5 to 95 mass % per total content of component (a).

Moreover, when component (a) contains a chain-type silicone (a3), the latter should be used in an amount of 0.5 to 95 mass % per total content of component (a).

The content of component (a) in a water-in-oil type emulsion cosmetic of the invention may be in the range of 0.1 to 95 mass %, and preferably in the range of 0.1 to 60 mass %.

If the content of component (a) is lower than the lower recommended limit (i.e., the content of an oiling agent is too low), this will be not only an obstacle for imparting excellent performance properties to a cosmetic product from the purified alkyl-modified silicone (a1) but also will not allow the emulsified cosmetic, itself, to fully demonstrate its performance characteristics. If, on the other hand, the content of component (a) exceeds 95 mass % (excessive content of the oiling agent), this will impair the good feeling of use.

<Component (b)>

A surface-active agent of the water-in-oil type emulsion cosmetic of the invention is the one that has the value of HLB (Hydrophile-Lipophile Balance) equal to or below 7. If the HLB value of the surface-active agent exceeds 7, the water-in-oil type emulsion cosmetic will have extremely high hydrophilic properties, and this will not allow obtaining a stable cosmetic.

The HLB value of a surface-active agent is calculated with the following formula:

$$HLB = A \times 0.89 + 1.11,$$

where "A" is the clouding point.

(Method of Measuring Clouding Point "A")

Clouding point "A" is measured as described below by the known method described by Ichiro Nishi in "Handbook of Surface-Active Agents", pp. 324 to 325 term, Sangyo Tosho Publishing Co., Ltd. (1965).

A 2.5-g dehydrated sample is weighed, and 98% ethanol is added (by using a 25-ml measuring flask) until the volume reaches 25 ml. Following this, 5 ml of the prepared mixture is taken by a transfer pipette, placed into a 50-ml beaker, and is stirred there at 25° C. by a magnetic stirrer during dropwise addition of a 2% phenolated aqueous solution by using a 25-ml burette. The terminal point of measurement is defined as the point at which the liquid becomes cloudy, and the amount of 2% phenol aqueous solution in units of ml, which is required for this titration, is designated as point "A" of clouding.

The surface-active agent that constitutes component (b) and has a value of HLB equal to or below 7 can be represented by the following compounds: sorbitan monolaurate, sorbitan monoisostearate, sorbitan tristearate, or similar sorbitan fatty acid esters; glycerol monostearate, glycerol monooleate, or similar glycerol fatty acid esters; POE (5) hydrogenated castor oil, POE (7.5) hydrogenated castor oil, and POE (10) hydrogenated castor oil, or a similar polyoxyethylene hydrogenated castor oil, polyether-modified silicone, etc. Most preferable is the polyether-modified silicone represented by general formula (6) given below:

General formula (6)

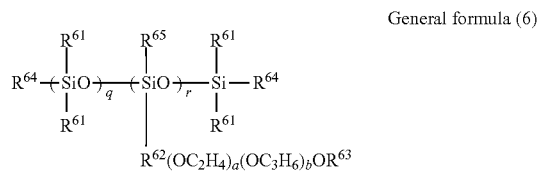

In general formula (6), each $R^{61}$ may independently designate a hydrogen atom or an optionally substituted or an unsubstituted univalent hydrocarbon group. Such optionally substituted or unsubstituted univalent hydrocarbon group may be represented by a methyl group, ethyl group, propyl group, or a similar alkyl group; a vinyl group, allyl group, or a similar alkenyl group; a phenyl group, tolyl group, xylyl group, or a similar aryl group; a benzyl group, phenethyl group, or a similar aralkyl group; a chloropropyl group, 3,3,3-trifluoropropyl group, or a similar halogenated alkyl group. The hydrogen atom or the methyl group is preferable.

In the above formula, $R^{62}$ represents a bivalent hydrocarbon group with 1 to 20 carbon atoms, preferably, 3 to 6 carbon atoms. Such hydrocarbon group may be exemplified by an alkylene group and an alkylene-arylene group. The alkylene group is preferable.

$R^{63}$ represents a hydrogen atom, a univalent hydrocarbon group, or an acetoxy group. More preferable are the following: a hydrogen atom, an alkyl group with 1 to 4 carbon atoms, or an acetoxy group, but most preferable are a hydrogen atom, a methyl group, or a butyl group.

In the above formula, "a" and "b" are numbers in the range of 0 to 60 which have an average value equal to or greater than 0.

$R^{64}$ and $R^{65}$ designate the same hydrogen atoms and optionally substituted univalent hydrocarbon groups that were defined for $R^{61}$, or designate —$R^{62}(OC_2H_4)_a (OC_3H_6) OR^{63}$ group; "q" is a number having an average value equal to or greater than 0; "q" is preferably in the range of 1 to 500; "r" is a number having an average value equal to or greater than 0; preferably in the range of 1 to 100.

In a molecule of the polyether-modified silicone, the aforementioned —$R^{62}(OC_2H_4)_a (OC_3H_6)OR^{63}$ group exists in an amount which on average is equal to or greater than 1. An average molecular weight of the aforementioned polyether-modified silicone is in the range of 250 to 1,000,000.

Polyether-modified silicone, which is most suitable for use as component (b), is the one where, in formula (6); $R^{61}$ is a hydrogen atom or a methyl group, "q" is a number having an average value in the range of 1 to 500, "r" is a number having an average value in the range of 1 to 100; and "a" and "b" are numbers having average values in the range of 0 to 35. A polyester-modified silicone having such a structure is produced by Nippon Unicar Co., Ltd. and is marketed as "SILWET SS-2805", "SILWET SS-2803".

The aforementioned surface-active agents having a value of HLB equal to or lower than 7 may be used as component (b), individually or in a mixture of two or more.

Generally, the content of component (b) in the water-in-oil type emulsion cosmetic of the present invention is in the range of 0.1 to 25 mass % and preferably in the range of 0.5 to 10 mass %.

If component (b) is contained in an amount less than the lower recommended limit, it would be impossible to obtain a composition required for preparing a stable emulsion. If, on the other hand, the content of component (b) exceeds the upper recommended limit, the obtained water-in-oil type emulsion cosmetic will become sticky and will lose the feel of freshness and good feel of use.

<Component (c)>

The water contained in the water-in-oil type emulsion cosmetic of the invention as component (c) constitutes mainly an internal phase (aqueous phase) and may comprise purified water suitable for use. Some water used as component (c) may exist in an external phase (oil phase).

Component (c) is usually contained in the water-in-oil type emulsion cosmetic of the invention in an amount of 4.9 to 95 mass %, preferably, 25 to 90 mass %, and most preferably, 50 to 90 mass %.

If the content of component (c) is below the lower recommended limit, it will be impossible to obtain a good feeling of use. If, on the other hand, the content of component (c)

exceeds the upper recommended limit, it will be difficult to obtain an emulsified cosmetic of high efficiency and performance.

The water-in-oil type emulsion cosmetic of the invention may contain an organically modified clay mineral. There are no special restrictions with regard to the organically modified clay mineral, and the one that normally is used in the preparation of cosmetic material may be added to the composition. The most preferable organically modified clay mineral is a cation-modified clay mineral treated with a water-expansive quaternary ammonium salt type surface-active agent.

The water-expansive quaternary ammonium salt type surface-active agent may be represented by stratified silicate-type mineral which belongs, for example, to a smectite group, and clay minerals, such as colloid-hydrated aluminum silicates having a three-layer structure and represented by general formula (7) given below:

$$(X,Y)_4(Si,Al)_4O_{10}(OH)_2Z_{1/3} \cdot nH_2O \qquad \text{General-formula (7)}$$

(where X designates Al, Fe(III), Mn(III), and Cr(III); Y designates Mg, Fe(II), Ni, Zn, and Li; Z designates K, Na, and Ca; and; "A" is a number in the range of 2 to 3).

Specifically, the aforementioned mineral may be comprised of a montmorillonite, saponite, hectorite, or a similar natural mineral, or a synthetic product of a montmorillonite group (where (OH) group in formula (7) is substituted with fluorine; such products are commercially known as Kunipia, Smecton (all products of Kunimine Industries Co., Ltd.; Veegum (the product of Banda Build Company), and Laponit (the product of Laporte Industries Ltd.)); sodium-silicic-mica sodium or lithium teniolit, or similar synthetic mica (commercially produced as Dymonite and fluoro-tetrasilicate mica by Topy Industries Co., Ltd.), etc. The aforementioned water-expansive clay minerals can be used individually or in a combination of two or more.

The quarternary-ammonium-salt type cationic surface-active agent used for treating the water-expansive clay mineral is a compound represented by the following general formula (8).

General-formula (8)

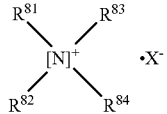

(where $R^{81}$ designates an alkyl group with 10 to 22 carbon atoms or a benzyl group; $R^{82}$ designates a methyl group or alkyl group with 10 to 22 carbon atoms, and, $R^{83}$ and $R^{84}$ independently designate alkyl groups with 1 to 3 carbon atoms or a hydroxyalkyl group with 1 to 3 carbon atoms. In the above formula, X designates a halogen atom or a residual methyl sulfate radical).

Specific examples of compounds of formula (8) are the following: dodecyl trimethylammonium chloride, myristyl trimethylammonium chloride, cetyl trimethylammonium chloride, stearyl trimethylammonium chloride, alkyl trimethylammonium chloride, behenyl trimethylammonium chloride, myristyl dimethylethyl ammonium chloride, cetyldimethyl ethylammonium chloride, stearyl dimethyl ethylammonium chloride, alkyldimethyl ethylammonium chloride, behenyl dimethyl ethylammonium chloride, myristyl diethyl methylammonium chloride, cetyl diethyl methylammonium chloride, stearyl diethyl methylammonium chloride, alkyl diethyl methylammonium chloride, behenyl diethyl methylammonium chloride, benzyl dimethyl myristyl ammonium chloride, benzyl dimethyl cetyl ammonium chloride, benzyl dimethyl stearyl ammonium chloride, benzyl dimethyl behenyl ammonium chloride, benzyl methylethyl cetyl ammonium chloride, benzyl methylethyl stearyl ammonium chloride, distearyl dimethyl ammonium chloride, dibehenyl dihydroxyethyl ammonium chloride, the same compounds as above where bromide is used instead of chloride, dipalmityl propylethylammonium methylsulfate, etc. One or several such quarternary-ammonium-salt type cationic surface-active agents can be selected for use.

The cationically modified clay type minerals treated with quarternary-ammonium-salt type cationic surface-active agents are commercially produced, e.g., as "Benton 38" (the product of National Red Co.), "Veegum Ultra" (produced by Vanderbilt Co.).

If necessary, in treating the water-expansive clay mineral, the aforementioned quarternary-ammonium-salt type cationic surface-active agent can be combined with a nonionic surface-active agent.

Such a nonionic surface-active agent can be represented by an ethylene-oxide-addition type surface-active agent, a polyhydric-alcohol fatty-acid-ester type surface-active agent, a nonionically modified surface-active agent, etc.

Specific examples of the aforementioned ethylene-oxide-addition type surface-active agent are the following: a polyoxyethylene 2 to 30 mole addition (hereinafter referred to as POE (2 to 30)) oleyl ether, POE (2 to 35) stearyl ether, POE (2 to 20) lauryl ether, POE (1 to 20) alkylphenyl ether, POE (6 to 18) behenyl ether, POE (5 to 25) 2-decylpentadecyl ether, POE (3 to 20) 2-decyltetradecyl ether, POE (3 to 20) 2-decyltetradecyl ether, POE (8 to 16) 2-octyldecyl ether, or a similar ethyl type surface-active agent; POE (4 to 60) hydrogenated castor oil, POE (3 to 14) fatty acid monoester, POE (6 to 30) fatty-acid diester, POE (5 to 20) sorbitan fatty-acid ether, or a similar ester type surface-active agent; POE (2 to 30) glyceryl monoisostearate, POE (10 to 60) glyceryl triisostearate, POE (7 to 50) hydrogenated-castor-oil monoisostearate, POE (12 to 60) hydrogenated-castor-oil triiso, or similar ether-ester-type surface active agents.

Specific examples of the polyhydric-alcohol fatty-acid-ester type surface active agent are the following: decaglyceryl tetraoleate, hexaglyceryl triisostearate, tetra-glyceryl diisostearate, diglyceryl diisostearate or similar polyglyceryl fatty acid esters, glyceryl monoisostearate, glyceryl monooleate, etc.

The nonionically modified silicone surface-active agent can be specifically exemplified by a dimethylpolysiloxane-polyoxyalkylene copolymer, or a similar modified silicone.

In addition to component (a), which is an oiling component, and an organically modified clay mineral (an arbitrary component) in the oil phase, which is an external (continuous) phase of the water-in-oil type emulsion cosmetic of the invention, the composition may also contain other arbitrary additives, provided that these additives are not detrimental to the effects of the present invention. For example, the aforementioned additives may comprise substances normally blended with conventional cosmetics, external therapeutic preparations, etc. They may comprise oil-soluble polymers, powders, granulated polymers, or the like.

Besides component (c), the aqueous phase, which is the internal phase of the water-in-oil type emulsion cosmetic of the invention, also may be combined with some arbitrary additives. Such components of the aqueous phase may comprise those additive that are normally used in conjunction with cosmetics, pharmaceutical substances, and therapeutic substances for external use, such as vitamin B group, vitamin C, their derivatives, pantothenic acid and its derivatives, biotin, and similar vitamins, or other water-soluble substances; sodium glutamate, arginine, aspartic acid, citric acid, tartaric acid, lactic acid, or similar buffering agents; EDTA, or similar chelating agents; water-soluble ultraviolet absorbants, various coloring agents, etc. These substances can be used without special restrictions.

The internal phase (aqueous phase) of the water-in-oil type emulsion cosmetic of the invention also may be comprised of an oil-in-water (O/W) type of emulsion prepared by dispersing microscopic particles of the oiling agent. The emulsified composition (O/W/O emulsion) having the above-described emulsion as an internal phase (dispersed particles) also is covered by the scope of the present invention.

In the range which is not detrimental to the effect of the present invention, the water-in-oil type of emulsion cosmetic of the present invention may be blended with a polyhydric alcohol, its derivative, and a moisturizing agent that improves the moisture-retaining effect.

The following are examples of the aforementioned polyhydric alcohols and their derivatives: ethylene glycol, propylene glycol, trimethylene glycol, 1,2-butylene glycol, 1,3-butylene glycol, tetramethylene glycol, 2,3-butylene glycol, pentamethylene glycol, 2-buten-1,4-diol, hexylene glycol, octylene glycol, or similar bifunctional alcohols; glycerol, trimethylol propane, 1,2,6-hexane triol, or similar trivalent alcohols; pentaerythritol or similar tetravalent alcohols; xylitol or similar pentavalent alcohols; sorbitol, mannitol, or similar hexavalent alcohols; diethylene glycol, dipropylene glycol, triethylene glycol, polypropylene glycol, triglycerol, tetraglycerol, polyglycerol, or similar polyvalent alcohol copolymers; ethylene glycol monomethyl ether, ethylene glycol monoethyl ether, ethylene glycol nomobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, or similar bivalent alcohol alkyl ethers; diethylene glycol monomethyl ether, diethylene glycol monoethyl ether, diethylene-glycol monobutyl ether, diethylene glycol, dimethyl ether, diethylene glycol diethyl ether, diethylene glycol dibutyl ether, diethylene glycol methylethyl ether, triethylene glycol monomethyl ether, triethylene glycol monoethyl ether, triethylene glycol monoethyl ether, propylene glycol monomethyl ether, propylene glycol monoethyl ether, propylene glycol monobutyl ether, propylene glycol monoisopropyl ether, dipropylene glycol methyl ether, dipropylene glycol ethyl ether, dipropylene glycol butyl ether, or similar bivalent alcohol alkyl ethers; ethylene glycol monomethyl ether acetate, ethylene glycol monoethyl ether acetate, ethylene glycol monobutyl ether acetate, ethylene glycol monophenyl ether acetate, ethylene glycol diadipate, ethylene disuccinate, ethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, or similar bivalent alcohol ethyl acetates; xylyl alcohol,
selachyl alcohol, batyl alcohol, or similar glycerol monoalkyl ethers; sorbitol, maltitol, maltotriose, mannitol, cane sugar, erythritol, glucose, fructose, starch-decomposition glucose, maltose, xylitose, starch-decomposition glucose-reduction alcohol, or similar sugar alcohols. The following alcohols also can be used in addition to the sugar alcohols: POE tetrahydrofurfuryl alcohol, POP butyl ether, POP•POE butyl ether, polyoxypropylene glycerol ether, POP glycerol ether, POP glycerol ether phosphoric acid, POP•POE pentaerythritol, etc.

A moisturizing agent can be represented by chondroitin sulfate, hyaluronic acid, mucoitinsulftiric acid, charonic acid, atelocollagen, cholesteryl-12-hydroxystearate, sodium lactate, bile acid monosalt, d1-pyrrolidone carboxylic acid mono salt, short-chain soluble collagen, Rosa Roxburghii Extract, Achillea Milefolium Extract, etc.

Within the limits which are not detrimental to the pleasant feel of use, the water-in-oil emulsion cosmetic of the invention can also be combined with various water-soluble polymers. Such polymers can be represented by natural, semisynthetic, or synthetic water-soluble polymers, as well as by inorganic water-soluble polymers.

The natural water-soluble polymers can be represented by gum arabic, tragacanth gum, galactan, guar gum, carob gum, karaya gum, carrageenan, pectin, agar agar, quince seed (marmelo), algae colloid (brown algae extract), starch (rice, corn, potato, and wheat), glycyrrhizic acid, or similar water-soluble polymers of vegetable origin; xanthan gum, dextran, succinoglucan, pullulan, casein, albumin, and gelatin, or similar water-soluble polymers of animal origin.

The aforementioned water-soluble polymers can be represented by carboxymethyl starch, methylhydroxypropyl starch, or similar starch-type water-soluble polymers; methyl cellulose, nitrocellulose, ethyl cellulose, methylhydroxypropyl cellulose, hydroxyethyl cellulose, cellulose sodium sulfate, hydroxypropyl cellulose, carboxymethyl cellulose sodium (CMC), crystalline cellulose, powdered cellulose, or similar cellulose-type water-soluble polymers; sodium alginate, propylene glycol alginate, alginic-acid propylene glycol ester, or similar alginic-acid-type water-soluble polymers.

Composite water-soluble polymers can be exemplified by polyvinyl alcohol, polyvinyl methyl ether, polyvinyl pyrrolidone, carboxyvinyl polymer (trade name "Carbopol"), or similar vinyl-type water-soluble-type polymers; polyethylene glycol with molecular weights 20,000, 4,000, and 6,000, or similar polyoxyethylene-type water-soluble polymers; polyoxyethylene polyoxypropylene copolymer-type water-soluble polymer; sodium polyacrylate, polyethylacrylate, polyacrylamide, or similar acryl-type water-soluble polymers; polyethyleneimine, cation polymer, etc.

The inorganic water-soluble polymer may be represented by bentonite, silicic acid AlMg (trade name "Veegum"), laponite, hectorite, silicic acid anhydride, etc.

Within the limits that are not detrimental to the effects of the present invention, besides the aforementioned additional components, the water-in-oil type of emulsion cosmetic may incorporate various anionic surface-active agents, nonionic surface-active agents, cationic surface-active agents, amphoteric surface-active agents, etc.

The water-in-oil type emulsion cosmetics of this invention may be used as skin cosmetics, hair cosmetics, or the like.

The water-in-oil type emulsion cosmetic of this invention can be manufactured according to conventional methods. For example, such a cosmetic can be prepared by uniformly mixing component (a) (i.e., oiling agent) that contains a purified product of alkyl-modified silicone (a1) with component (b) (surface-active agent), thus obtaining a preliminary mixture, which, when stirred, is combined with gradually added water as component (c), and then the obtained mixture is uniformly stirred.

If necessary, other arbitrary components can be added either to the aforementioned preliminary mixture or to the product after emulsification.

EXAMPLES

The invention will now be described in more detail with reference to the Practical Examples, which, however, should not be construed as limiting the scope of the invention application.

Practical Example 1

(1) Step [A]

A reactor made of glass and equipped with a stirrer, a reflux condenser, a thermometer, and nitrogen feeding pipe was loaded with 1000 parts by mass of 1,1,1,3,5,5,5-heptamethyltrisiloxane and 0.100 parts by mass of a 10% ethanol solution of a chloroplatinic acid (catalyst). The components were stirred during heating, and after the liquid reached the stable temperature of 74° C., a dropwise addition of 1-octene was initiated. The resulting hydrosilylation reaction caused generation of heat. The total amount (555 parts by mass) of 1-octene was added dropwise while adjusting the rate of feed so that solution temperature would not exceed 120° C. Upon completion of the dropwise addition, stirring was discontinued. One hour later, the reaction mixture was sampled, the sample was mixed with an aqueous/ethanol solution of potassium hydroxide, and the hydrosilylation reaction was determined to be complete when the generation of hydrogen was discontinued.

Subsequently, sodium bicarbonate was added to the reaction mixture (85° C.) in the amount of 1.55 parts by mass, and neutralization was carried out by stirring the mixture for 30 minutes.

The interior of the reactor was decompressed along with the supply of gaseous nitrogen, the temperature was increased to 120° C., and the low-boiling-point components (light components) were removed by distillation (stripping step) for the duration of 1 hour at a pressure of 1.3 kPa.

The obtained reaction product was cooled to room temperature, atmospheric pressure was restored, and the product was mixed with 10 parts by mass of diatomaceous earth and was subjected to pressurized filtration, whereby solid matter was separated (separation of the catalyst). The filtrate comprised 1300 parts by mass of a crude product of a liquid medium-chain alkyl-modified polydimethylsiloxane (hereinafter referred to as a "crude product (1A)") represented by formula (i), given below.

After manufacture, the obtained crude product (1A) looked like a uniform, slightly yellow transparent liquid that did not have any unpleasant odor.

Chemical Formula (i)

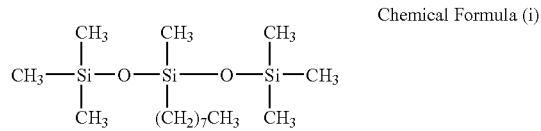

(2) Step [B]

A stainless steel autoclave having a 1-liter capacity and equipped with an electromagnetic stirrer was loaded with 400 parts by mass of crude product (1A), 16 parts by mass of a Raney nickel catalyst, 26 parts by mass of THF, and 0.5 parts by mass of purified water. After the gaseous interior (gaseous phase) was completely replaced with gaseous hydrogen, the pressure of the hydrogen was raised to 8.0 MPa. While the contents of the system were stirred, they were gradually heated, and then deodorization was performed by a hydrogenation reaction that was carried out for 6 hours at 140° C.

(3) Post-Treatment Step (Separation of Catalyst and Stripping)

The reaction product obtained from Step [B] was cooled to 60° C., and hydrogen was blown out and replaced with gaseous nitrogen.

Subsequently, the Raney nickel catalyst was removed from the reaction product by pressurized filtration.

The obtained filtrate was loaded into a 1 liter-capacity two-neck flask equipped with a reflux condenser and a nitrogen-supply pipe. During supply of nitrogen, the interior of the flask was evacuated, the temperature was raised to 120° C., components with low boiling points (light substances) were removed for the duration of 1 hour under a pressure of 1.3 KPa, and filtrate was concentrated to produce 350 parts by mass of a purified product of a liquid medium-chain alkyl-modified polydimethylsiloxane (hereinafter referred to as "purified product (1B)") of aforementioned chemical formula (i).

Practical Example 2

(1) Step [A]

2120 parts by mass of a purified product ("crude product (2A)") of a liquid medium-chain alkyl-modified polydimethylsiloxane of chemical formula (ii) given below were produced by means of the same hydrosilylation reaction, neutralization treatment, removal of low-boiling-point substances, and filtration of solid matter (removal of the catalyst) as in Step [A] of Practical Example 1, with the exception that 1360 parts by mass of 1-octadecene were used instead of 1 octene.

The obtained crude product (2A) had the appearance of a uniform, slightly yellow transparent liquid, which after post-treatment did not have an unpleasant odor.

Chemical Formula (ii)

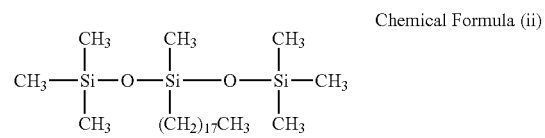

(2) Step [B]

The deodorization procedure by hydrogenation was performed similar to Step [B] of Practical Example 1, except that 400 parts by mass of crude product (2A) were used instead of crude product (1A).

(3) Post-Treatment Step (Separation of Catalyst and Stripping)

Post-treatment of the reaction product obtained from Step [B] was carried out similar to the corresponding process of Practical Example 1 (separation of the catalyst and stripping), whereby 345 parts by mass of a purified product of a liquid medium-chain alkyl-modified polydimethylsiloxane (hereinafter referred to as "purified product (2B)") of aforementioned chemical formula (ii) were obtained.

The obtained purified product (2B) had the appearance of a uniform, colorless, transparent liquid, which did not have an unpleasant scent and comprised a practically odorless product.

Practical Example 3

(1) Step [A]

1150 parts by mass of a purified product ("crude product (3A)") of a liquid medium-chain alkyl-modified polydimethylsiloxane of chemical formula (iv) given below were produced by means of the same hydrosilylation reaction, neutralization treatment, removal of low-boiling-point substances, and filtration of solid matter (removal of the catalyst) as in Step [A] of Practical Example 1, with the exception that 278 parts by mass of 1-dodecene were used instead of 1-octane and that 1000 parts by mass of a hydrosilyl-containing polydimethylsiloxane of chemical formula (iii), given below, were used instead of 1,1,1,3,5,5,5-heptamethyltrisiloxane.

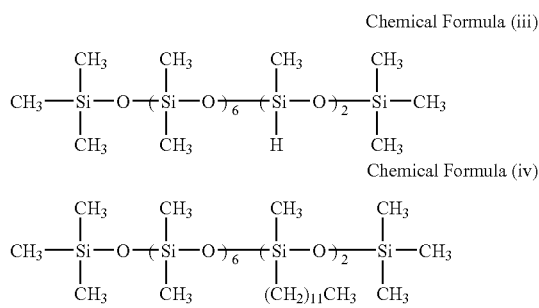

(2) Step [B]

The deodorization procedure by hydrogenation was performed similar to Step [B] of Practical Example 1, except that 400 parts by mass of crude product (3A) were used instead of crude product (1A).

(3) Post-Treatment Step (Separation of Catalyst and Stripping)

Post-treatment of the reaction product obtained from Step [B] was carried out similar to the corresponding process of Practical Example 1 (separation of the catalyst and stripping), whereby 350 parts by mass of a purified product of a liquid medium-chain alkyl-modified polydimethylsiloxane (hereinafter referred to as "purified product (3B)") of aforementioned chemical formula (iv) were obtained.

The obtained purified product (3B) had the appearance of a uniform, colorless transparent liquid, which after post-treatment did not have an unpleasant scent and comprised a practically odorless product.

[Evaluation of Odor with Time]

The purified products (1B) to (3B) and non-deodorized crude products (1A) to (3A) obtained in Practical Examples 1 to 3 were sealed in containers. After the contents of the containers were kept sealed for 30 days at 70° C., the containers were opened, and the contents were evaluated with regard to the presence and degree of odor.

The results of the evaluation showed that in the purified product the unpleasant odor was practically absent and did not appear with the lapse of time.

In contrast to the purified products, the crude products (1A) to (3A) produced a strong, unpleasant odor that increased with the passage of time.

Practical Example 4

Moisturizing Cream

An oiling-phase component (an oiling agent with arbitrary components) was obtained by uniformly mixing components (6) to (11) and component (13) in the proportions shown below. In a separate operation, component (1) was combined with components (2), (4), and (5). The obtained mixture was compounded with component (12) and dissolved in component (3), whereby an aqueous-phase component was produced. The obtained aqueous-phase component was combined with the oiling-phase component. Emulsification particles were adjusted by uniformly treating the product in a homogenizing mixer, and, as result, a moisturizing cream comprising a water-in-oil type emulsion cosmetic of the present invention was prepared.

[Composition]
(1) Purified water: balance
(2) Glycine: 1.0 mass %
(3) 1,3-butyleneglycol: 5.0 mass %
(4) Trehalose: 3.0 mass %
(5) "Dynamite" glycerol: 5.0 mass %
(6) Purified product of alkyl-modified silicone (a1) comprised of purified product (1B) obtained in Practical Example 1: 10.0 mass %
(7) Decamethyl cyclopentasiloxane: 6.0 mass %
(8) Octamethylcyclotetrasiloxane: 4.0 mass %
(9) Polyester-modified silicone having HLB=5.00 and represented by aforementioned general formula (6) (where $R^{61}$, $R^{64}$, and $R^{65}$ are methyl groups, $R^{62}$ is an alkylene group with 3 carbon atoms, $R^{63}$ is a hydrogen atom, "a"=8, "b"=0, "q"=80, and "r"=5): 2.0 mass %
(10) Organically modified clay mineral "Benton 27" (National Red Company): 3.0 mass %
(11) Vitamin E-acetate: 1.0 mass %
(12) Methylparaben: optimum dose
(13) Perfume: optimum dose Practical Example 5

A moisturizing cream comprising a water-in-oil type emulsion cosmetic of the present invention was prepared in the same manner as in Practical Example 4, except that the aforementioned component of item (6) was replaced by 10 mass % of the alkyl-modified silicone (a1) obtained from purified product (2B) of Practical Example 2.

Practical Example 6

A moisturizing cream comprising a water-in-oil type emulsion cosmetic of the present invention was prepared in the same manner as in Practical Example 4, except that the aforementioned component of item (6) was replaced by 10 mass % of the alkyl-modified silicone (a1) obtained from purified product (3B) of Practical Example 3.

The moisturizing creams (water-in-oil type emulsion cosmetics of the invention) obtained according to Practical Examples 4 to 6 possessed excellent feeling of use (freshness and cleanliness), showed the effect of protecting makeup from spreading and deterioration, demonstrated excellent water repellency, stability at high temperatures, and excellent preservation stability in a wide range of temperatures (−10 to 40° C.).

Practical Example 7

O/W/O Type Cream

After preparing an O/W emulsion from components (1) to (10) in accordance with the composition given below, the aforementioned O/W emulsion was added to an oiling-phase component prepared by uniformly dispersing components (11) to (15) and uniformly dispersed in it by means of a dispersion mixer to produce a cream in the form of an O/W/O type emulsion. The obtained emulsion demonstrated good stability and excellent feeling of use.

[Composition]
(1) Polyoxyethylene hydrogenated castor oil: 2.0 mass %
(2) Behenyl alcohol: 6.0 mass %
(3) Liquid paraffin: 12.0 mass %
(4) Vaseline: 3.0 mass %
(5) Vitamin E-acetate: 1.0 mass %
(6) Ion exchange water: balance
(7) 1,3 butylene-glycol: 5.0 mass %
(8) Ascorbic acid: 0.5 mass %
(9) Arbutin: 2.0 mass %
(10) Phenoxyethanol: optimum dose
(11) Polyester-modified silicone having HLB=3.5 and represented by aforementioned general formula (6) (where $R^{61}$, $R^{64}$, and $R^{65}$ are methyl groups, $R^{62}$ is an alkylene group with 3 carbon atoms, $R^{63}$ is a hydrogen atom, "a"=10, "b"=4, "q"=300, and "r"=10): 2.0 mass %
(12) Organically modified clay mineral "Benton 38" (National Red Company): 3.0 mass %
(13) Decamethyl cyclopentasiloxane: 3.0 mass %
(14) Purified product of alkyl-modified silicone (a1) prepared from a purified product (1B) obtained in Practical Example 1: 8.0 mass %
(15) Perfume: optimum dose

Practical Example 8

A cream that comprised an O/W/O emulsion was prepared in the same manner as in Practical Example 7, except that component (14) was replaced by 8.0 mass % of the purified product (a1) of the alkyl-modified silicone prepared from purified product (2B) of Practical Example 2.

Practical Example 9

A cream that comprised an O/W/O emulsion was prepared in the same manner as in Practical Example 7, except that component (14) was replaced by 8.0 mass % of the purified product (a1) of the alkyl-modified silicone prepared from purified product (3B) of Practical Example 3.

The creams (water-in-oil type emulsion cosmetics of the invention) obtained according to Practical Examples 7 to 9 possessed excellent feeling of use (freshness and cleanliness), showed the effect of protecting the makeup from spreading and deterioration, and demonstrated excellent water repellency, stability at high temperatures, and excellent preservation stability in a wide range of temperatures (−10 to 40° C.).

Practical Example 10

W/O Type Sun-Screening Agent

Oiling-phase components (1) to (5) were mixed in accordance with the composition given below, and the mixture was heated to 55° C. In a separate process, a mixture was prepared from aqueous-phase components (6) to (12), and the prepared mixture was heated to 55° C. Under conditions of slow stirring, the aforementioned aqueous-phase component mixture was added dropwise to the oiling-phase component mixture. When the addition of the aqueous-phase component was completed, the product was slowly cooled to 40° C. and stirred. As a result, a sun-screening agent was prepared as a stable W/O type emulsion.

[Composition]
(1) Decamethyl cyclopentasiloxane: 9.5 mass %
(2) Polyester-modified silicone having the HLB value of 2.5 and expressed by formula (6) given above (where $R^{61}$, $R^{64}$, and $R^{65}$ are methyl groups, $R^{62}$ is an alkylene group with 3 carbon atoms, $R^{63}$ is a hydrogen atom, "a"=10, "b"=0, "q"=400, and "r"=8): 3.5 mass %
(3) Isopropyl lanolate: 1.0 mass %
(4) Lanolin alcohol/mineral oil: 3.5 mass %
(5) Purified product of alkyl-modified silicone (a1) obtained from purified product (B1) of Practical Example 1: 2.0 mass %
(6) Purified water: balance
(7) Propylene glycol: 5.0 mass %
(8) Sodium chloride: 0.8 mass %
(9) Carboxyvinyl polymer: 0.3 mass %
(10) pH-adjusting agent: optimum dose
(11) Antiseptics: optimum dose
(12) Perfume: optimum dose

Practical Example 11

A sun-screening agent that constitutes a W/O-type emulsion was obtained in the same manner as in Practical Example 10, except that 2.0 mass % of the purified product (a1) of the component of Item (5) were replaced by the alkyl-modified silicone (a1) obtained from the purified product (2B) of Practical Example 2.

Practical Example 12

A sun-screening agent that constitutes a W/O-type emulsion was obtained in the same manner as in Practical Example 10, except that 2.0 mass % of the purifies product (a1) of the component of Item (5) were replaced by the alkyl-modified silicone (a1) obtained from the purified product (3B) of Practical Example 3.

The sun-screening agents (water-in-oil type emulsion cosmetics of the invention) obtained according to Practical Examples 10 to 12 possessed excellent feeling of use (freshness and cleanliness), showed the effect of protecting the cosmetics from spreading and deterioration, and demonstrated excellent water repellency, stability at high temperatures, and excellent preservation stability in a wide range of temperatures (−10 to 40° C.).

Practical Example 13

W/O-Type Sun-Screening Agent

Oiling-phase components (1) to (10) were mixed in accordance with the composition given below, and the mixture was heated to 65 to 70° C. In a separate process, a mixture was prepared from aqueous-phase components (11) to (12), and the prepared mixture was heated to 65 to 70° C. Under conditions of slow stirring, the aforementioned aqueous-phase component mixture was added dropwise to the oiling-phase component mixture. When the addition of the aqueous-phase component was completed, the product was slowly cooled to 25° C. and stirred. As a result, a sun-screening agent was prepared as a stable W/O type emulsion.

[Composition]
(1) Highly polymerized dimethylpolysiloxane (in the form of a gum): 1.0 mass %
(2) Decamethyl cyclopentasiloxane: 12.0 mass %
(3) Purified product of alkyl-modified silicone (a1) prepared from the product of purification (1B) obtained in Practical Example 1: 12.0 mass %
(4) Polyester-modified silicone having the HLB value of 6.0 and expressed by formula (6) given above (where $R^{61}$, $R^{64}$, and $R^{65}$ are methyl groups, $R^{62}$ is an alkylene group with 3 carbon atoms, $R^{63}$ is a hydrogen atom, "a"=7, "b"=0, "q"=85, and "r"=8): 1.5 mass %
(5) Lanolin alcohol: 0.75 mass %
(6) Glyceryl monostearate: 1.75 mass %
(7) Dipropylene glycol: 5.0 mass %
(8) Polyester-modified silicone having the HLB value of 1.0 and expressed by formula (6) given above (where $R^{61}$, $R^{64}$, and $R^{65}$ are methyl groups, $R^{62}$ is an alkylene group with 3 carbon atoms, $R^{63}$ is a butyl group, "a"=0, "b"=13, "q"=4, and "r"=2): 3.0 mass %
(9) Titanium oxide (MT-100 Tayca Co., Ltd.): 8.0 mass %
(10) Paraben: 0.2 mass %
(11) Purified water: 54.6 mass %
(12) Sodium chloride: 0.2 mass %

Practical Example 14

A sun-screening agent that constitutes a W/O-type emulsion was obtained in the same manner as in Practical Example 13, except that 12.0 mass % of the purified product (a1) of the component of Item (3) were replaced by the alkyl-modified silicone (a1) obtained from the purified product (2B) of Practical Example 2.

Practical Example 15

A sun-screening agent that constitutes a W/O-type emulsion was obtained in the same manner as in Practical Example 13, except that 12.0 mass % of the purifies product (a1) of the component of Item (3) were replaced by the allyl-modified silicone (a1) obtained from the purified product (3B) of Practical Example 3.

The sun-screening agents (water-in-oil type emulsion cosmetics of the invention) obtained according to Practical Examples 13 to 15 possessed excellent feeling of use (freshness and cleanliness), showed the effect of protecting the cosmetics from spreading and deterioration, and demonstrated excellent water repellency, stability at high temperatures, and excellent preservation stability in a wide range of temperatures (−10 to 40° C.).

INDUSTRIAL APPLICABILITY

The method of the invention makes it possible to prepare a purified product of a liquid medium-chain alkyl-modified polydimethylsiloxane that does not have an unpleasant odor and is practically odorless.

The purified product obtained by the method of the invention can be used in the manufacture of cosmetic, external therapeutic substances, and therapeutic drugs as a constituent of skin cosmetics, hair cosmetics, external skin preparations, etc.

The invention claimed is:
1. A method of manufacturing a purified product of a liquid medium-chain, alkyl-modified polydimethylsiloxane comprising the steps of:
[A] synthesizing a liquid medium-chain alkyl-modified polydimethylsiloxane represented by general formula (2) by carrying out a hydrosilylation reaction between a hydrosilyl-containing polydimethylsiloxane of general formula (1) and an α-olefin with 4 to 12 carbon atoms; and
[B] subjecting a crude product of the liquid medium-chain alkyl-modified polydimethylsiloxane obtained in preceding step [A] to an odor-removing treatment by conducting a hydrogenation reaction which is carried out in the presence of a hydrogenation catalyst:

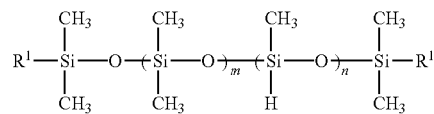

General Formula (1)

where $R^1$ represents a hydrogen atom or a methyl group; "m" is an integer from 0 to 6; and "n" is an integer from 0 to 3; however, when "n" is 0, then at least one $R^1$ represents a hydrogen atom,

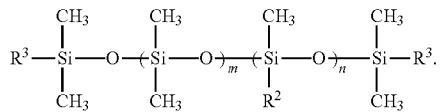

General Formula (2)

where $R^2$ represents an alkyl group with 4 to 12 carbon atoms; $R^3$ are groups represented by $R^2$ above or a methyl group; and "m" and "n" are the same numbers as defined above for general formula (1); however, when "n" is 0, at least one $R^3$ is the same group as defined for $R^2$.

2. The method of manufacturing a purified product of a liquid medium-chain alkyl-modified polydimethylsiloxane according to claim 1 wherein in step [A] a liquid medium-chain alkyl-modified polydimethylsiloxane of general formula (3) is synthesized by conducting a hydrosilylation reaction between 1,1,1,3,5,5,5-heptamethyltrisiloxane and an α-olefin having 4 to 12 carbon atoms:

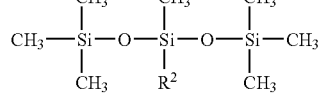

General Formula (3)

where $R^2$ is the same as defined above for general formula (2).

3. The method of manufacturing a purified product of a liquid medium-chain alkyl-modified polydimethylsiloxane according to claim 2 further comprising a step of stripping a crude product of the liquid medium-chain alkyl-modified polydimethylsiloxane and/or a product of hydrogenation from light substances prior to and/or after step [B] by bringing the crude product of the liquid medium-chain alkyl-modified polydimethylsiloxane and/or a product of hydrogenation in contact with gaseous nitrogen under conditions of reduced pressure.

4. A cosmetic material that contains a purified product of the liquid medium-chain alkyl-modified polydimethylsiloxane produced by the method according to claim 3.

5. A cosmetic material prepared from a water-in-oil emulsion having an oiling agent in the form of a purified product of the liquid medium-chain alkyl-modified polydimethylsiloxane produced by the method according to claim 3.

6. A cosmetic material prepared from a water-in-oil emulsion comprising: (a) 0.1 to 95 mass % of an oiling agent which is the liquid medium-chain alkyl-modified polydimethylsiloxane obtained by the method according to claim 3; (b) 0.1 to 25 mass % of a surface-active agent with the value of HLB equal to or below 7; and (c) 4.9 to 95 mass % of water.

7. A cosmetic material that contains a purified product of the liquid medium-chain alkyl-modified polydimethylsiloxane produced by the method according to claim 2.

8. A cosmetic material prepared from a water-in-oil emulsion having an oiling agent in the form of a purified product of the liquid medium-chain alkyl-modified polydimethylsiloxane produced by the method according to claim 2.

9. A cosmetic material prepared from a water-in-oil emulsion comprising: (a) 0.1 to 95 mass % of an oiling agent which is the liquid medium-chain alkyl-modified polydimethylsiloxane obtained by the method according to claims 2; (b) 0.1 to 25 mass % of a surface-active agent with the value of HLB equal to or below 7; and (c) 4.9 to 95 mass % of water.

10. The method of manufacturing a purified product of a liquid medium-chain alkyl-modified polydimethylsiloxane according to claim 1 further comprising a step of stripping a crude product of the liquid medium-chain alkyl-modified polydimethylsiloxane and/or a product of hydrogenation from light substances prior to and/or after step [B] by bringing the crude product of the liquid medium-chain alkyl-modified polydimethylsiloxane and/or a product of hydrogenation in contact with gaseous nitrogen under conditions of reduced pressure.

11. A cosmetic material that contains a purified product of the liquid medium-chain alkyl-modified polydimethylsiloxane produced by the method according to claim 10.

12. A cosmetic material prepared from a water-in-oil emulsion having an oiling agent in the form of a purified product of the liquid medium-chain alkyl-modified polydimethylsiloxane produced by the method according to claim 10.

13. A cosmetic material prepared from a water-in-oil emulsion comprising: (a) 0.1 to 95 mass % of an oiling agent which is the liquid medium-chain alkyl-modified polydimethylsiloxane obtained by the method according to claim 10; (b) 0.1 to 25 mass % of a surface-active agent with the value of HLB equal to or below 7; and (c) 4.9 to 95 mass % of water.

14. A cosmetic material that contains a purified product of the liquid medium-chain alkyl-modified polydimethylsiloxane produced by the method according to claim 1.

15. A cosmetic material prepared from a water-in-oil emulsion having an oiling agent in the form of a purified product of the liquid medium-chain alkyl-modified polydimethylsiloxane produced by the method according to claim 1.

16. A cosmetic material prepared from a water-in-oil emulsion comprising:
   (a) 0.1 to 95 mass % of an oiling agent which is the liquid medium-chain alkyl-modified polydimethylsiloxane obtained by the method according to claims 1; (b) 0.1 to 25 mass % of a surface-active agent with the value of HLB equal to or below 7; and (c) 4.9 to 95 mass % of water.

17. A method of manufacturing a purified product of a liquid medium-chain alkyl-modified polydimethylsiloxane comprising the steps of:
   [A] synthesizing a liquid medium-chain alkyl-modified polydimethylsiloxane represented by general formula (3) by carrying out a hydrosilylation reaction between 1,1,1,3,5,5,5-heptamethyltrisiloxane and an α-olefin with 6 to 12 carbon atoms; and
   [B] subjecting a crude product of the liquid medium-chain alkyl-modified polydimethylsiloxane obtained in preceding step [A] to an odor-removing treatment by conducting a hydrogenation reaction which is carried out in the presence of a hydrogenation catalyst:

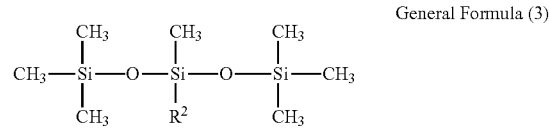

General Formula (3)

where $R^2$ represents an alkyl group with 6 to 12 carbon atoms.

* * * * *